US007226472B2

(12) United States Patent
Pederson, Jr. et al.

(10) Patent No.: US 7,226,472 B2
(45) Date of Patent: Jun. 5, 2007

(54) CATHETER BALLOON WITH ADVANTAGEOUS CONE DESIGN

(75) Inventors: Gary John Pederson, Jr., Albertville, MN (US); Jan D. Seppala, Maple Grove, MN (US); John Robert Moberg, Elk River, MN (US); Steven Paul Mertens, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 433 days.

(21) Appl. No.: 10/271,524

(22) Filed: Oct. 15, 2002

(65) Prior Publication Data

US 2004/0073250 A1 Apr. 15, 2004
US 2005/0203563 A9 Sep. 15, 2005

(51) Int. Cl.
*A61F 2/06* (2006.01)
(52) U.S. Cl. ...................................... 623/1.11
(58) Field of Classification Search ............... 623/1.11, 623/1.12, 1.15; 606/108, 192, 194, 195, 606/198
See application file for complete search history.

(56) References Cited

U.S. PATENT DOCUMENTS

| 4,490,421 | A | 12/1984 | Levy ........................... 428/35 |
| 4,950,227 | A | 8/1990 | Savin et al. .................... 604/8 |
| 4,950,239 | A | 8/1990 | Gahara et al. .................. 604/96 |
| 5,195,969 | A | 3/1993 | Wang et al. .................... 604/96 |
| 5,270,086 | A | 12/1993 | Hamlin ....................... 428/35.2 |
| 5,556,383 | A | 9/1996 | Wang et al. .................... 604/96 |
| 5,733,301 | A | 3/1998 | Forman ........................ 606/192 |
| 5,944,726 | A | 8/1999 | Blaeser et al. ............... 606/108 |
| 5,980,530 | A | 11/1999 | Willard et al. ............... 606/108 |
| 6,168,748 | B1 | 1/2001 | Wang et al. .................. 264/520 |
| 6,210,364 | B1 | 4/2001 | Anderson et al. ......... 604/96.01 |
| 6,328,710 | B1 | 12/2001 | Wang et al. .............. 604/96.01 |
| 6,383,212 | B2 * | 5/2002 | Durcan et al. .............. 623/1.11 |
| 6,409,741 | B1 | 6/2002 | Crocker et al. ............. 606/192 |
| 6,764,504 | B2 * | 7/2004 | Wang et al. ................ 623/1.11 |
| 2001/0000350 | A1 | 4/2001 | Durcan et al. ............. 623/1.11 |
| 2002/0077690 | A1 | 6/2002 | Wang ........................ 623/1.11 |

FOREIGN PATENT DOCUMENTS

| EP | 1 062 966 A | 12/2000 |
| JP | 2000 051361 | 2/2000 |

* cited by examiner

*Primary Examiner*—Kevin T. Truong
(74) *Attorney, Agent, or Firm*—Vidas, Arrett, Steinkraus

(57) ABSTRACT

The present invention provides a catheter balloon having an advantageous cone design. In particular, the catheter balloon has at least one cone section with a volume in $mm^3$ such that, when the ratio of one cone volume to the transverse cross-sectional area in $mm^2$ of the inflated median section is at least about 2.1 mm. In certain applications, the advantageous cone design can assist in the preferential expansion of the cone sections prior to any significant expansion of the median section. The balloon can thus advantageously be utilized as a component of a balloon catheter or prosthesis delivery system, also provided via the present invention. When so utilized, the inventive balloon can assist in reducing any shifting of the balloon and/or prosthesis during inflation or delivery, respectively. Methods of utilizing the balloon catheters in dilation procedures, as well as the prosthesis delivery systems to deliver prosthesis, are also provided.

17 Claims, 5 Drawing Sheets

CATHETER BALLOON WITH ADVANTAGEOUS CONE DESIGN

FIELD OF THE INVENTION

The present invention pertains generally to catheter balloons useful in medical dilation and stent delivery procedures. More specifically, the present invention relates to catheter balloons wherein the cone sections have a design that, in some applications, can provide the cone sections with the ability to preferentially inflate relative to the median section of the catheter balloon.

BACKGROUND OF THE INVENTION

Angioplasty is a widely utilized therapeutic treatment in which obstructed intraluminal passages are reopened or dilated. In a typical procedure, a catheter comprising an inflatable member, such as a balloon, is inserted percutaneously into a luminal passage of a patient, such as an artery, vein, airway, etc. Once inserted, the balloon is advanced to the desired treatment site, where the balloon may be inflated to dilate the luminal passage. In certain applications, the balloon catheter may be used to place an intravascular prosthesis, such as a stent, within the luminal passage, which prosthesis could then operate to maintain the patency of the luminal passage.

Although vascular angioplasty and stenting are widely utilized and largely successful procedures, improvements to the same could yet be made. In dilation procedures, for example, it would be desirable for the inflatable member to controllably inflate, and at times preferentially inflate, to better control the position of the inflatable member. In procedures wherein an intravascular prosthesis is to be delivered, it would be desirable to enhance the robustness of the delivery of the prosthetic device.

SUMMARY OF THE INVENTION

The invention is generally directed to catheter balloons including cone sections having an advantageous design. In particular, the cone sections have a ratio of the volume of one cone section to the transverse cross-sectional area of the fully inflated median section that can provide for a more controlled inflation of the balloon. In certain applications, such as the delivery of a prosthesis from a catheter comprising the balloon, this cone configuration can assist in the preferential expansion of the cones prior to the median section of the balloon. Such a preferential expansion can further act to control the position of the implantable device. In such prosthesis delivery systems where socks or sleeves are desirably employed, the utilization of the inventive balloon can be particularly advantageous. In particular, the preferential expansion of the cone sections of the inventive balloon prior to the median section can aid in the release of the stent from such socks or sleeves.

In a first aspect, then, the invention provides a catheter balloon, and a method of forming the inventive catheter balloon. The catheter balloon generally has expandable cone sections proximal and distal to a median section of the balloon. When the balloon is filly inflated, the median section has a transverse cross sectional area, and each cone section has a volume, so that the ratio of the volume, in $mm^3$, of either of the cone sections to the transverse cross sectional area, in $mm^2$, of the median section is at least about 2.1 mm. Although this ratio, and the measurements utilized in calculating the ratio, is/are expressed in millimeters, the measurements can be taken in any units and the ratio calculated, so long as the measurements or the resulting ratio are converted to the units of millimeters by applying the appropriate conversion factor.

It has now been discovered that one way of providing a cone section with a sufficient volume to provide the aforementioned advantageous ratio is to provide the cone section with a stepped configuration having a plurality of sections, wherein at least one of the sections defines an internal angle relative to the median section of greater than 180 degrees. Thus, in an additional aspect, the invention provides a catheter balloon having cone sections proximal and distal to a median section of the balloon. At least one of the cone sections has a stepped configuration comprising a plurality of sections, wherein at least one of the sections defines an internal angle relative to the median section of greater than about 180 degrees.

In a further aspect, the invention provides a balloon catheter and method of manufacturing the same. The balloon catheter generally comprises a catheter having an elongated shaft with an inflatable catheter balloon on a distal section of the catheter shaft. The catheter balloon generally has expandable cone sections proximal and distal to a median section of the balloon. When the balloon is fully inflated, the median section has a transverse cross sectional area in $mm^2$, and each cone section has a volume, in $mm^3$, so that the ratio of the volume of either of the cone sections to the transverse cross sectional area of the median section is at least about 2.1 mm.

A further aspect of the invention provides a stent delivery system, the stent delivery system generally comprising a balloon catheter wherein the balloon catheter has an elongated shaft with an inflatable balloon on a distal section of the catheter shaft. The catheter balloon generally has expandable cone sections proximal and distal to a median section of the balloon. When the balloon is fully inflated, the median section has a transverse cross sectional area in $mm^2$, and each cone section has a volume in $mm^3$, so that the ratio of the volume of either of the cone sections to the transverse cross sectional area of the median section is at least about 2.1 mm. An expandable stent is operatively disposed about at least a portion of the median section of the catheter balloon.

Advantageously, the catheter balloon of the present invention can aid in the retraction of sleeves or socks in stent delivery systems including such sleeves or socks. Optionally, then, the stent delivery system may further comprise at least one such sleeve or sock. The sleeve can be provided having a first end mounted on the distal shaft section distal to the catheter balloon and a second end defining a margin between the stent and the sleeve, wherein the sleeve overlies the margin between the stent and the median section when the catheter balloon is substantially uninflated.

The inventive catheter balloon, when utilized as a component of an angioplasty catheter or a stent delivery system can provide for the improved performance thereof. When used in combination with a stent delivery system, for example, the inventive cone design can assist in the preferential expansion of the cone sections. This preferential expansion can reduce any shifting of the stent during delivery that may otherwise occur. As a result, the present invention additionally provides methods of dilating a bodily lumen, or for delivering a stent. The methods comprise the steps of providing a balloon catheter or stent delivery system embodying features of the present invention, inserting the balloon catheter, or stent delivery system, as the case may be, into a bodily lumen and inflating the balloon so that the median section expands to dilate the bodily lumen and/or to deliver the stent.

These and other advantages of the invention will become more apparent from the following detailed description of the invention and the accompanying exemplary drawings.

BRIEF DESCRIPTION OF THE DRAWINGS

The accompanying drawings, which are incorporated in and constitute a part of this application, illustrate several aspects of the invention and together with descriptions of the illustrated embodiments serve to explain the principles of the invention. A brief description of the drawings is as follows.

DETAILED DESCRIPTION

The embodiments of the present invention described below are not intended to be exhaustive or to limit the invention to the particular embodiments disclosed in the following detailed description. Rather, the embodiments are described so that others skilled in the art can understand the principles and practices of the present invention.

The present invention provides balloons suitable for use in catheters comprising cone sections having an advantageous design. In particular, the inventive catheter balloon has cone sections having a volume so that the ratio of the volume of one cone (in $mm^3$) to the transverse cross sectional area of the fully inflated median section (in $mm^2$) is at least about 2.1 mm. Although this ratio, and the measurements utilized in calculating the ratio, is/are expressed in millimeters, the measurements can be taken in any units and the ratio calculated, so long as the measurements or the resulting ratio are converted to the units of millimeters by applying the appropriate conversion factor.

It has now been discovered that catheter balloons having such cone sections can be more controllably inflated, and in certain applications, can provide preferential expansion of the cone sections prior to any significant expansion of the median section of the balloon. Balloons having such a cone design can be utilized in balloon catheters or prosthesis delivery systems where this capability can act to reduce any shifting of the prosthesis during expansion and delivery thereof that may otherwise occur.

Figure 1:
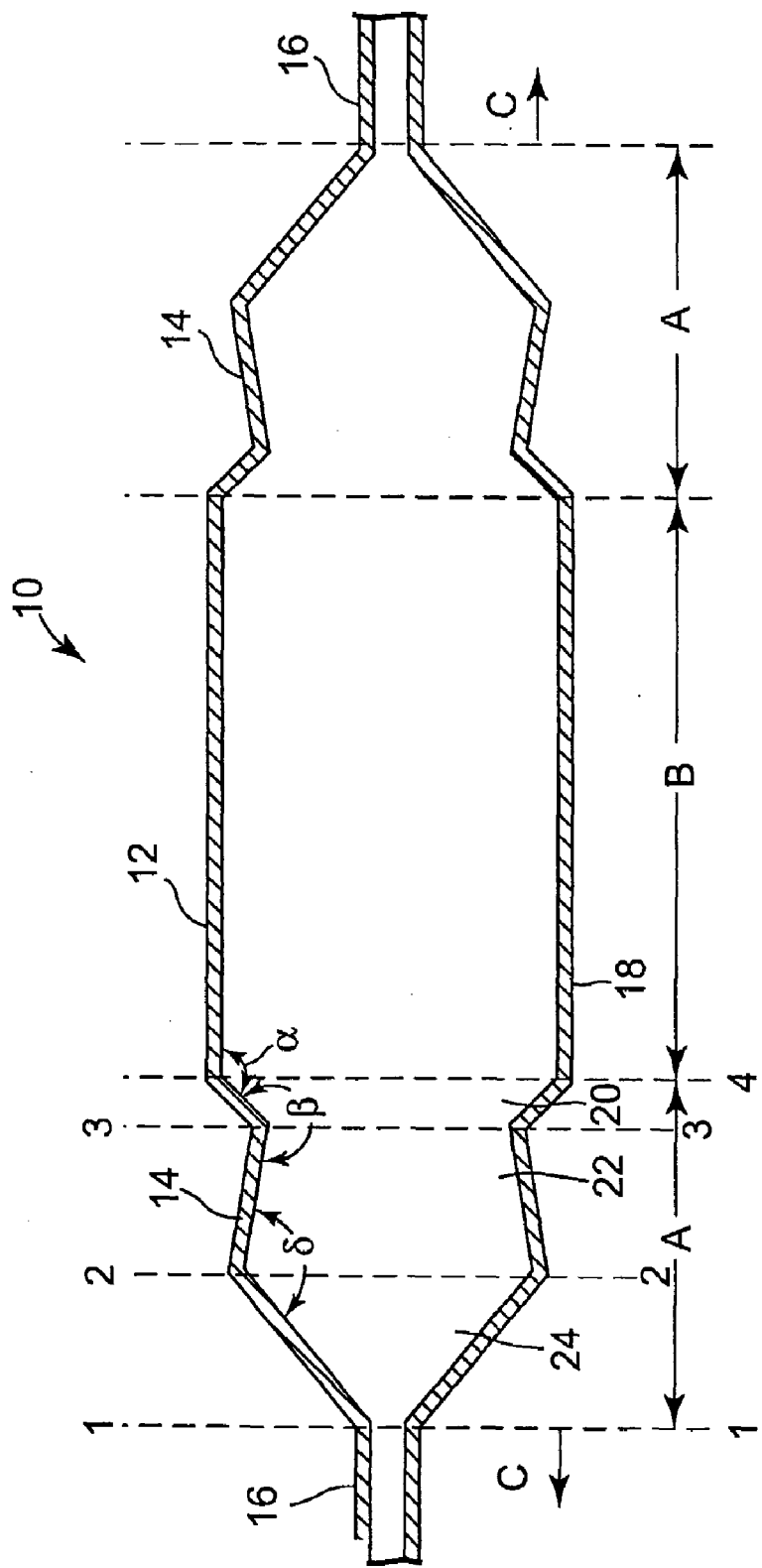
FIG. 1 is a longitudinal cross-sectional view of a catheter balloon embodying features of the present invention.

One exemplary catheter balloon embodying features of the invention is shown in FIG. 1. Specifically, FIG. 1 illustrates, in cross-sectional side view, an expanded inflatable balloon 10. Inflatable balloon 10 is described, for purposes of illustrating the design features of the invention, as having at least three regions.

A first region is the centermost section, or the median section 12 of balloon 10, and is indicated by 'B' in FIG. 1. Median section 12, when inflated, runs generally parallel with, and engages, a patient's luminal passage, such as a vessel wall, or inner diameter of a stent. Median section 12 can comprise the majority of the length of inflatable balloon 10, and typically has the greatest diameter of the three regions when balloon 10 is fully inflated.

Second regions of balloon 10 are comprised of the waists 16 on the first and second ends of balloon 10. Waists 16 are used to adhere balloon 10 to one or a more catheter shafts (not shown). Waists 16 are indicated by 'C' in FIG. 1.

Third regions, indicated by 'A' in FIG. 1, are comprised of the cone sections 14 of balloon 10 provided between the median section 12 and the waists 16. As illustrated in FIG. 1, inflatable balloon 10 includes a single median section 12, proximal and distal cone sections 14 and proximal and distal waists 16. However, other configurations are possible and are within the scope of the present invention. As examples, other regions can be provided between the described sections 12, 14 and 16 to perform other functions.

Cone sections 14 include a first section 20, defined by lines 3—3 and 4—4, a second section 22, defined by lines 2—2 and 3—3, and a third section 24, defined by lines 1—1 and 2—2. First section 20 is proximal to median section 12, and forms a first angle α relative to median section 12. First angle α is desirably between about 90° and about 180°. Second section 22 is proximal to first section 20 and forms an angle β relative to first section 20 as shown. Angle β is desirably between about 180° and 360°, typically between about 180° and 270°. Third section 24 is proximal to second section 22 and forms an angle δ relative to second section 22 that is desirably between about 30° and 180°.

It has now been discovered that, by providing a preselected ratio of the volume of one cone section 14 to the transverse cross sectional area of fully inflated median section 12, a catheter balloon 10 can be produced that can provide a more controllable inflation that balloons not having the preselected ratio. More particularly, it has now been discovered that when the ratio of the volume of one cone section 14 (in $mm^3$) to the transverse cross-sectional area of the fully inflated median section 12 (in $mm^2$) is at least about 2.1 mm, preferably at least about 2.25 mm, more preferably, at least about 2.5 mm, the advantages of the present invention can be seen. Of course, and as mentioned above, the volume and transverse cross-sectional area measurements can be taken, and the ratio of the same calculated, in any units, so long as the units of either both of the measurements, or the calculated ratio, are mathematically converted to millimeters via application of the appropriate conversion factor.

It is believed that there is no maximum to this ratio, since, in general, a greater ratio suggests a more controllable inflation of the cone sections 14. The ratio can be, for example, 3.0 mm, 3.5 mm, 4.0 mm, 4.5 mm, 5.0 mm, etc. However, and for purposes of illustration only, it is believed that the inventive relationship is particularly advantageous when the ratio of the volume of one cone section 14 (in mm$^3$) to the transverse cross sectional area of fully inflated median section 12 (in mm$^2$) is from about 2.1 mm to about 4.0 mm, more preferably from about 2.1 mm to about 2.5 mm.

The volume and/or shape of cone sections 14 on either side of median section 12 need not be identical, so long as the specified ratio can be achieved utilizing the volume of at least one cone section. That is, although the embodiment illustrated in FIG. 1 of balloon 10 is symmetrical and median section 12 is at a central location on the balloon, alternative balloon designs may be used for particular applications and anatomies. Additionally, the inventive concept can be applied to any size catheter balloon 10, so long as the advantageous ratio of the volume of one cone section 14 to the transverse cross sectional area of the median section 12 is provided.

Finally, shape or geometry of cone sections 14 is not critical, and although a stepped cone configuration is illustrated in FIG. 1, cone sections 14 need not exhibit this configuration. Rather, cone sections 14 can be stepped, tapered or any other suitable configuration, as long as the ratio of the volume of one cone section 14 (in mm$^3$) to the transverse cross sectional area of fully inflated median section 12 (in mm$^2$) is at least about 2.1 mm.

Figure 2:
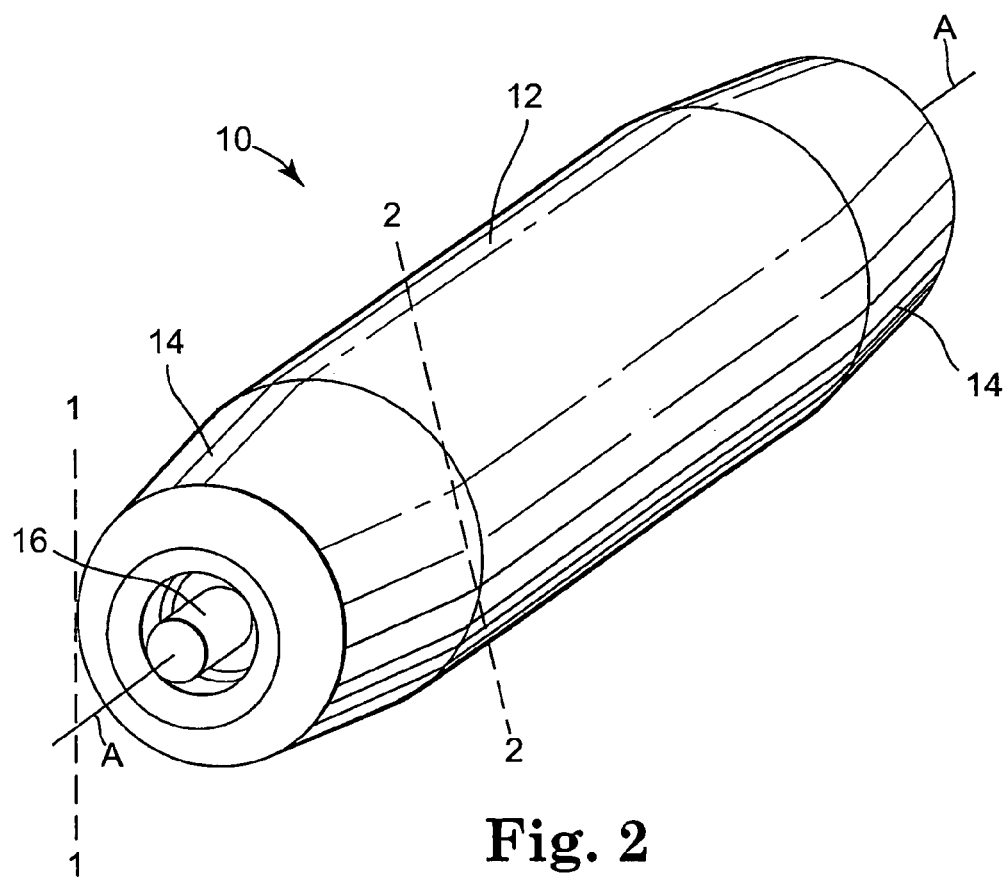
FIG. 2 is a schematic, perspective view of a further catheter balloon embodying features of the present invention.
Figure 2A:
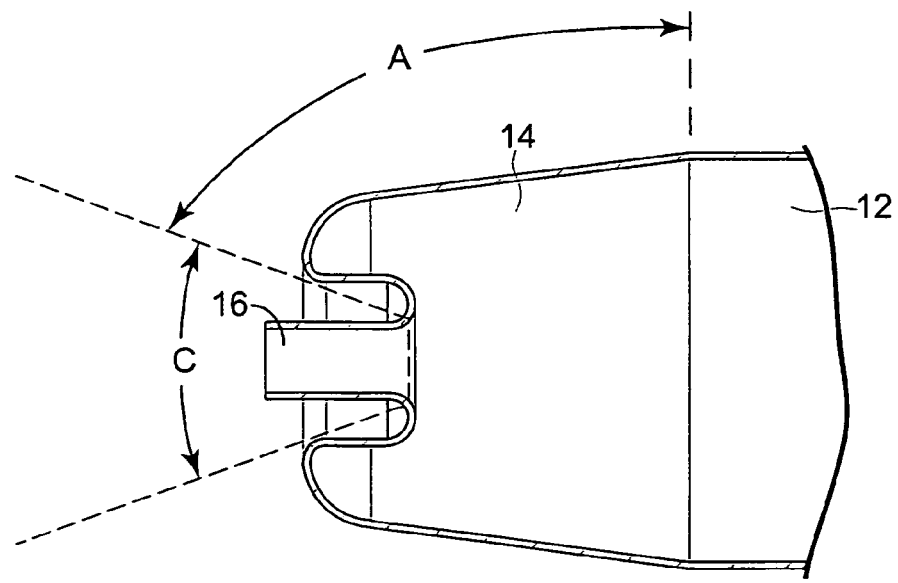
FIG. 2A is a longitudinal, partial cross-sectional view of the catheter balloon of FIG. 2, wherein the view provided is as between lines 1—1 and 2—2 of the balloon at FIG. 2, and the cross section is taken at line A—A.

In this regard, an additional suitable balloon configuration embodying features of the present invention is shown in FIGS. 2 and 2A. In particular, FIG. 2 shows a balloon catheter wherein the balloon includes 'bulged' cone sections 14 in addition to waists 16 and median section 12. In particular, waists 16 are indicated by 'C' in FIG. 2A. Cone sections 14 are indicated by 'A' in FIG. 2A and are provided between median section 12 and waists 16.

Cone volume and cross sectional area can be easily calculated for all cone and balloon geometries based on known mathematical formulas and are calculated based upon the balloon 10 when median section 12, or median section 12 and one or both of cone sections 14, is/are fully inflated. As used and discussed herein, all measurements and calculations were made and carried out in dimensions of millimeters. For example, if cone sections 14 are tapered, cone volume of cone sections would be calculated based on the cumulative volume of the defined geometric 3D shapes. Generally, tapering cone sections 14 provides cone sections with right circular cone geometry, for which volume can be calculated by applying the formula $V=(\frac{1}{3})\pi r^2 h$. If cone sections are stepped, as is shown in FIG. 1, cone volume would be calculated using the same formula as above, applied to two areas defined by the intervening angle(s). That is, the cone volume of the cone defined by lines 1—1 and 2—2, by lines 2—2 and 3—3 and by lines 3—3 and 4—4 would be calculated and added together to obtain the volume of one cone section 14 of balloon 10. The volume of cone sections 14 can be further easily determined by filling cone sections 14 with water, and weighing the water.

The transverse cross sectional area of median section 12 is calculated based upon median section 12 when fully inflated and can be calculated using the known mathematical formula $A=\pi r^2$.

Also, as performed in connection with the present application, transverse cross sectional area and cone volume are calculated as indicated above, regardless of any other parts and/or substances that may be introduced into the cone sections 14 or median section 12 once the balloon has been formed. That is, if catheter balloon 10 is to be included on a balloon catheter, as shown in FIG. 2, the volume of cone sections 14, or transverse cross-sectional area of median section 12, would be calculated without reducing the calculated volume or cross sectional area by that volume or cross sectional area that is taken up by, e.g., an inner tubular member and an outer tubular member, not shown in FIG. 2 once the balloon catheter has been assembled. Further, the wall thickness of the balloon is assumed to be negligible, i.e., the calculations of cross-sectional area and volume that were performed were based upon the outer diameter of the respective balloon sections.

The catheter balloon of the present invention can be produced by any suitable technique, including conventional techniques for producing catheter balloons. For example, a catheter balloon embodying features of the present invention can be formed by molding. In order to mold the balloon illustrated in FIG. 1, or any other balloon within the scope of the invention, an extruded polymeric tube can be radially expanded and axially expanded within a mold generally having the desired shape of the balloon at elevated temperatures. The resulting balloon may be heat treated one or more times as is conventionally known, e.g., to reduce shrinkage of the balloon. Non-limiting examples of methods for manufacturing balloons are disclosed in U.S. Pat. Nos. 4,950,239; 4,490,421; 5,195,969; 5,556,383; 6,210,364; 5,270,086; and 6,168,748.

Catheter balloon 10 may be formed from any material, or combination of materials, typically used to form catheter balloons. The particular material(s) chosen will depend upon the intended use of the catheter balloon. In those uses in which a compliant material is desired, low pressure, relatively soft or flexible polymeric materials such a thermoplastic polymers, thermoplastic elastomers, polyethylene (high density, low density, intermediate density, linear low density), various co-polymers and blends of polyethylene, ionomers, polyesters, polyurethanes and polyurethane copolymers (such as, e.g., Pellethane®), polycarbonates, polyamides (such as, e.g., Nylon 12), poly-vinyl chloride, acrylonitrile-butadiene-styrene copolymers, polyether-polyester copolymers (such as, e.g., Hytrel® and Arnitel®), and polyether-polyamide copolymers (such as, e.g., Pebax®) are useful. When a non-compliant balloon material is desired, materials having relatively rigid properties such as poly (ethylene terphthalate), polyimide, thermoplastic polyimide, polyamides, polyesters, polycarbonates, polyphenylene sulfides, polypropylene and rigid polyurethanes are useful.

As mentioned above, catheter balloon 10 may be comprised of a combination of materials, and may be coextruded, single layered or multilayered. Catheter balloon 10 may further be coated with any known suitable coating, if desired. Such coatings may be desirable, for example, in those applications where a lubricious balloon surface is desired.

The balloon material may further be crosslinked or uncrosslinked, depending upon the nature of the material and the characteristics desired for a particular application. Generally speaking, crosslinking a balloon material can result in greater control over the final inflated balloon size. That is, after crosslinking, initial pressurization, expansion, and preshrinking, a balloon so treated may thereafter expand in a more controlled manner to a reproducible diameter in response to a given inflation pressure, relative to an uncrosslinked balloon comprising similar material. If desired, crosslinking can be performed by any conventional crosslinking process, such as, for example, thermal treatment and/or E-beam exposure.

Once formed, the thickness of any portion of balloon wall 18, shown in FIG. 1, may be varied if desired. Varied balloon thickness can be useful, for example, in order to facilitate folding of balloon 10 around a catheter shaft to achieve a desired low profile, or to achieve various balloon pressure ratings. Material may be added, removed or combinations thereof to achieve the desired result. Typically, varying the thickness of balloon wall 18 is desired in median section 12 and/or cone sections 14 of balloon 10. Exemplary means of modifying the thickness of the cone sections of a balloon are disclosed in commonly assigned U.S. Pat. No. 5,733,301, the entirety of which is hereby incorporated by reference herein for all purposes.

Figure 3:
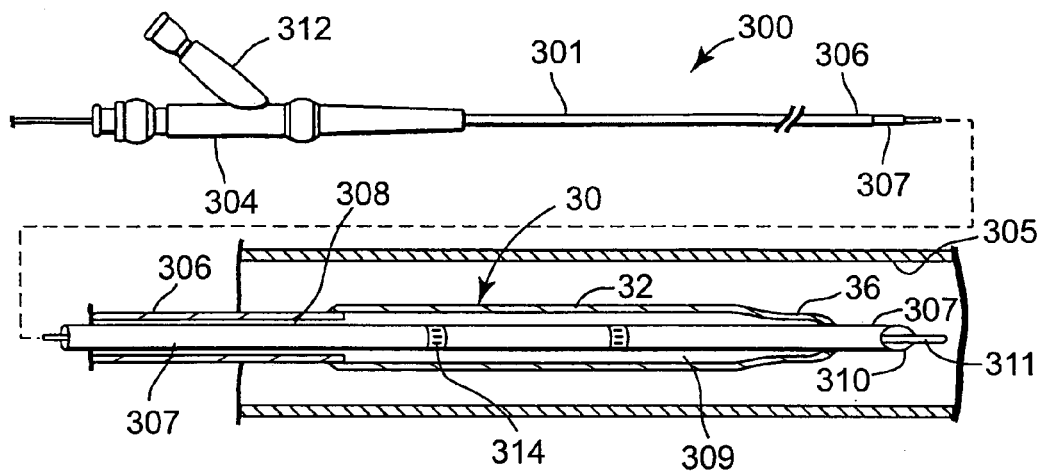
FIG. 3 is an elevational view, partially in section, of a balloon catheter embodying features of the present invention, wherein the balloon is in an unexpanded state.

FIG. 3 illustrates a balloon catheter embodying features and advantages of the invention. Balloon catheter 300 generally includes an elongated catheter shaft 301 having proximal section 302 and distal section 303, an inflatable balloon 30 disposed on the distal section 303 of catheter shaft 301, and manifold 304 mounted on proximal section 302 of shaft 301 to permit controllable sliding over guidewire 311 and for fluid introduction within shaft 301. Radiopaque markers 314 may be provided on catheter shaft 301, as for example, on inner tubular member 307 near the proximal and distal ends of median section 32 of balloon 30. In FIG. 3, balloon catheter 300 is illustrated within a patient's body lumen 305 prior to expansion of balloon 30, i.e., with balloon 30 in a low profile, unexpanded state for advancement within the patient.

In the embodiment illustrated, catheter shaft 301 has an outer tubular member 306 and an inner tubular member 307 disposed within outer tubular member 306, and defining along with outer tubular member 306, inflation lumen 308. Inflation lumen 308 is in fluid communication with the interior chamber 309 of inflatable balloon 30. Inner tubular member 307 has an inner lumen 310 extending therethrough to slidably receive a guidewire 311 suitable for advancement through a patient's body lumen 305. The distal extremity of inflatable balloon 30 is sealingly secured to the distal extremity of inner tubular member 307 and the proximal extremity of the balloon 30 is sealingly secured to the distal extremity of the outer tubular member 306. Balloon 30 can be inflated by any fluid, e.g., radiopaque, injected through inflation port 312, or otherwise provided through inflation lumen 308, or by other means, such as from a passageway formed between the outside of the catheter shaft and the member forming balloon 30, depending on the particular design of the catheter. The details and mechanics of fluid transfer and introduction within balloons vary according to the specific design of the catheter, and are well know in the art.

Various designs for balloon catheters are well known in the art, and all of these and other developed balloon catheters may incorporate the balloon features of the present invention. Examples include over-the-wire catheters, single operator or rapid exchange catheters, and fixed-wire catheters, to name a few. Further, catheter shaft 301, and the outer tubular member 306 and inner tubular member 307 incorporated therein, can have the dimensions of any conventional dilatation or stent delivery catheters, and inner and outer tubular members incorporated into the same. Shaft diameters of conventional catheter shafts generally range e.g., from about 4 to about 15 French.

Figure 4:
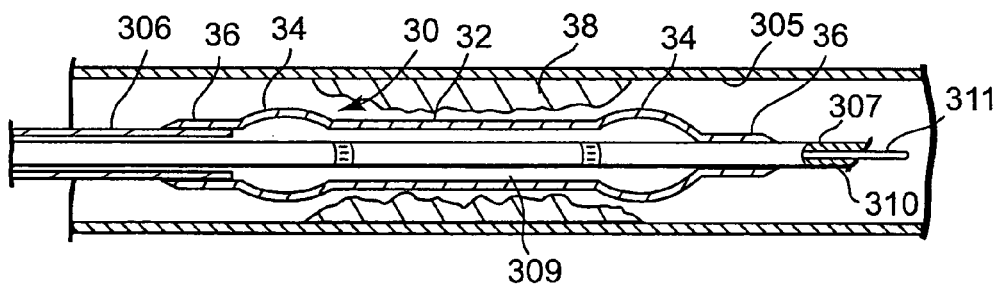
FIG. 4 is a cross-sectional view of the balloon catheter shown in FIG. 3, depicting the balloon partially expanded.
Figure 5:
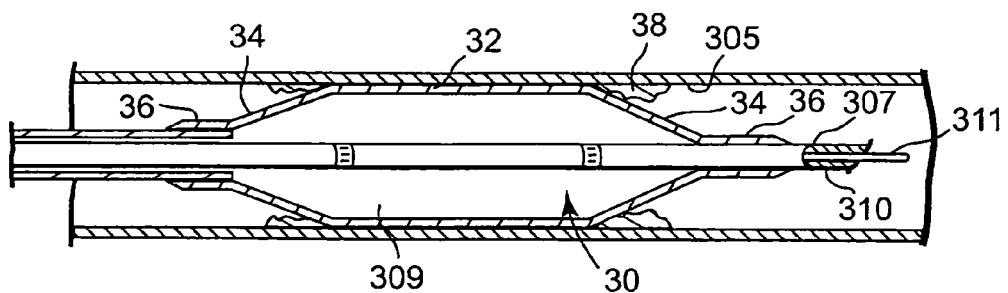
FIG. 5 is a cross-sectional view of the balloon catheter shown in FIG. 3, depicting the balloon fully expanded.

FIGS. 4 and 5 illustrate the advantages that can be seen incorporating the inventive balloon 30 into balloon catheter 300 and then utilizing balloon catheter 300 in a treatment procedure. In particular, FIG. 4 shows inflatable balloon 30 placed within lesion 38 located within a bodily lumen 305 and partially inflated. FIG. 5 shows inflatable balloon 30 fully inflated so as to be dilating lesion 38 within bodily lumen 305.

Referring in particular to FIG. 4, balloon 30 includes median section 32 centrally located on balloon 30 and cone sections 34 adjacent to the proximal and distal ends of median section 32. As shown, cone sections 34 taper or curve to join waists 36, but may be of any other geometry. Waist 36 of balloon 30 distal to median section 32 is sealingly secured to inner tubular member 307 while waist 36 of balloon 30 proximal to median section 32 is sealingly secured to outer tubular member 306, using any suitable means, such as adhesive and/or fusion bonding.

Figure 6:
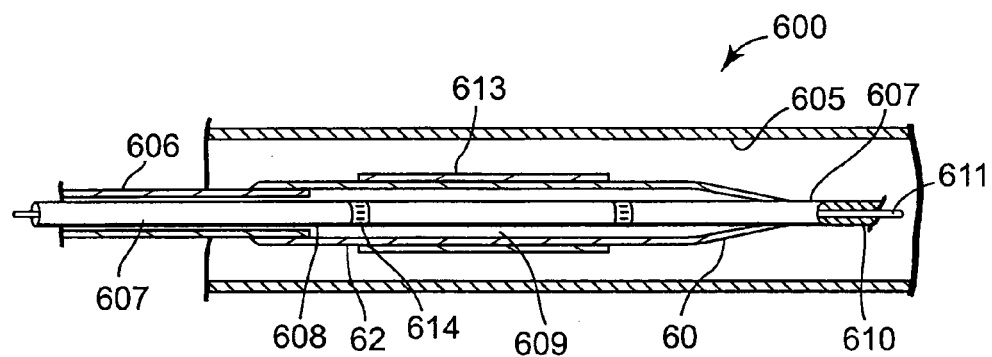
FIG. 6 is a cross-sectional view of a stent delivery system utilizing a balloon and embodying features of the present invention, wherein the balloon is in an unexpanded state.
Figure 7:
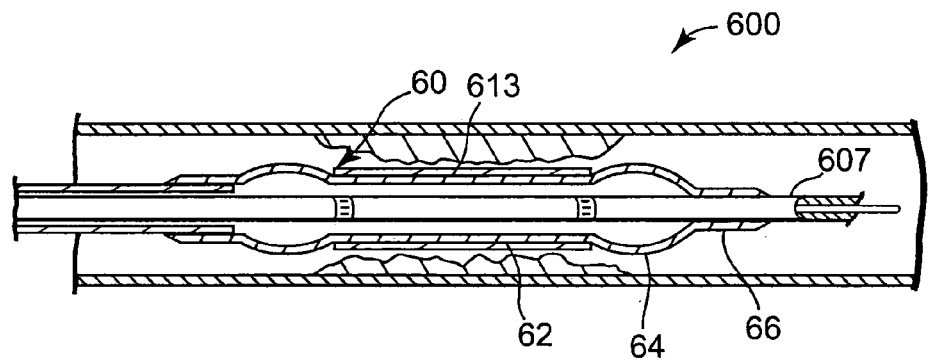
FIG. 7 is a cross-sectional view of the stent delivery system shown in FIG. 6, depicting the balloon partially expanded.
Figure 8:
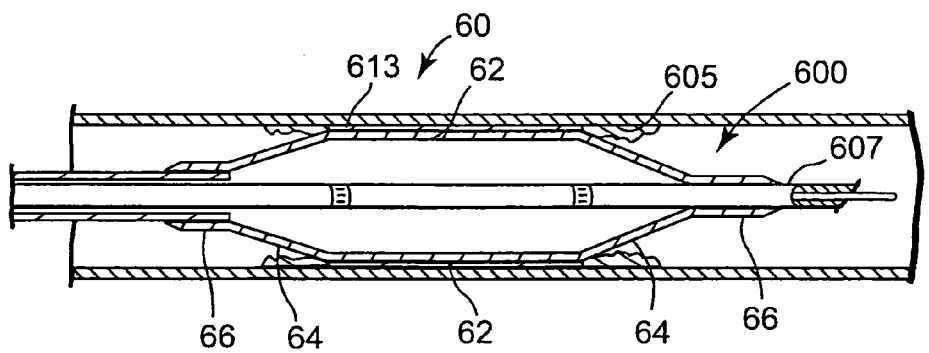
FIG. 8 is a cross-sectional view of the stent delivery system shown in FIG. 6, depicting the balloon and stent expanded.

Turning now to FIGS. 6–8, there is illustrated a stent delivery system 600 embodying features of the invention. The stent delivery system illustrated can be largely identical to the balloon catheter discussed above in connection with FIG. 2, and like features and the relationships between features will not be discussed further, as a description thereof can be found hereinabove.

Referring in particular to FIG. 6, balloon 60 has stent 613 mounted thereon in order to form stent delivery system 600. Stent delivery system 600 is illustrated within a patient's body lumen 605, prior to expansion of balloon 60, with balloon 60 and stent 613 in a low profile, unexpanded state for advancement within the patient.

FIG. 7 shows balloon 60 partially inflated at a first, low pressure. Partial inflation of balloon 60 causes the inflation of cone sections 64, without causing significant expansion of median section 62, or stent 613 mounted on median section 62. When so partially inflated, median section 62 remains in a deflated, low profile configuration, while cone sections 64 have expanded to an inflated outer diameter greater than that of the outer diameter of median section 62 and stent 613.

As is best illustrated by FIG. 8, when the inflation pressure is increased, median section 62 expands against the vessel wall 605, thereby expanding stent 613 mounted thereon. In this position, stent 613 is fully deployed and capable of maintaining the patency of lumen 605. Advantageously, and due at least in part to the preferential expansion of cone sections 64, any potential shifting of stent 613 within lumen 605 that may have otherwise occurred can be reduced, and as a result, a more robust stent delivery can be obtained.

Stent 613 may be mounted onto balloon 60 by any known method, e.g., by causing stent 613 to contract, by folding or wrapping stent 613 around and onto balloon 60, by crimping stent 613 onto balloon 60, either by hand or with a crimping tool, or by any other known method. Stent 613 may also be formed of non-knitted material so that the axial length of stent 613 decreases as stent 613 expands, thus enhancing the release of stent 613 from stent delivery system 600. Further, stent 613 may be any kind of stent, including plastically deformable or elastically deformable stents, or may be a superelastic stent. Finally, stent 613 may be formed with different knitting parameters, wall thicknesses, loop size or may be formed from of any of a variety of stent materials. For example, stent 613 may be comprised of stainless steel, titanium, niobium, tantalum, a nickel-titanium alloy, any other suitable metallic alloy, a plastic material, or various other materials. Stent 613 may additionally be coated with a film or membrane if desired.

Figure 9:
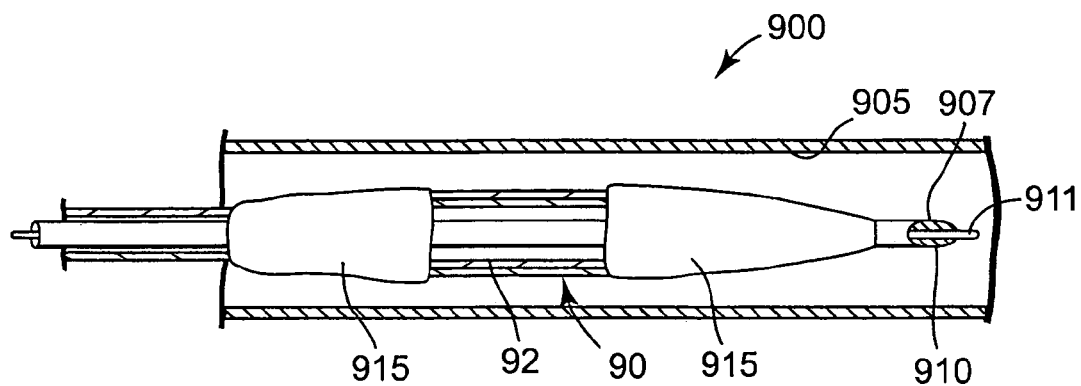
FIG. 9 is a cross-sectional view of another stent delivery system utilizing a balloon and embodying features of the present invention, wherein the balloon is in an unexpanded state and the stent delivery system comprises sleeves.
Figure 10:
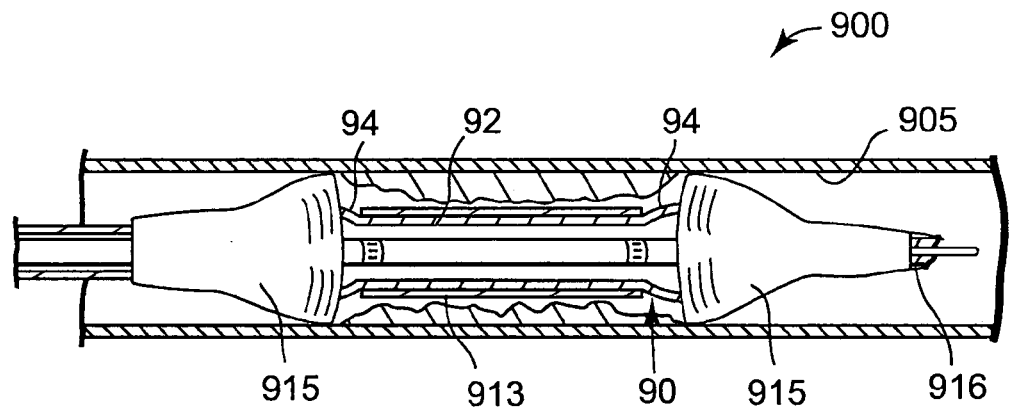
FIG. 10 is a cross-sectional view of the stent delivery system shown in FIG. 9, depicting the balloon partially expanded.
Figure 11:
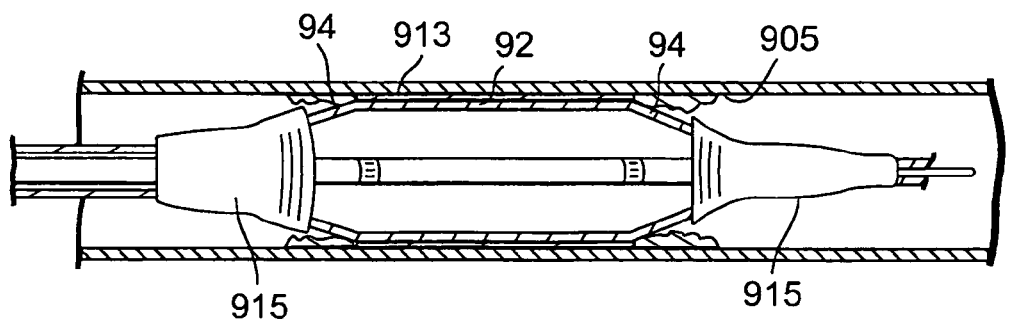
FIG. 11 is a cross-sectional view of the stent delivery system shown in FIG. 9, depicting the balloon and stent expanded.

FIGS. 9–11 illustrate a further stent delivery system embodying features of the invention. The balloon catheter upon which stent 913 is mounted to form stent delivery system 900 can be largely identical to that described in connection with FIG. 3 hereinabove, and will not be substantially described further in connection with FIGS. 9–11.

Referring to FIG. 9, stent delivery system 900 includes a balloon catheter, including balloon 90, which may be attached to the catheter by any known procedure. Balloon 90 is shown in its contracted state in FIG. 9. Stent 913 is held in position about median section 92 of balloon 90 by two sleeves, 915. As discussed above, stent 913 may be formed of any suitable material and of a length and circumference suitable for the intended use. Stent 913 is radially compressed against median section 92 of balloon 90 to provide a compressed diameter, suitable for insertion and advancement within a patient. Sleeves 915 are axially fixed on the catheter at one end, e.g., as by adhesive, thermal bonding, etc., and at the other end, overlap stent 913 at each end or margin, of stent 913. Although shown with two sleeves 915, stent delivery system 900 may be provided with only one sleeve 915.

FIG. 10 shows balloon 90 partially inflated at a first, low pressure. The first pressure causes the inflation of cone sections 94, without causing significant expansion of median section 92 or stent 913 mounted on median section 92. The inflation of cone sections 94, in turn, drives sleeves 915 away from the median section 92 and to release the margins of stent 913 from under sleeves 915. When so partially inflated, median section 92 remains in a deflated, low profile configuration, and stent 913 remains in its unexpanded state, while cone sections 94 have expanded to an inflated outer diameter greater than that of the outer diameter of median section 92 and stent 913. Preferably cones inflate to expand size of median section 92 of balloon 90 and to contact body lumen.

Referring to FIG. 11, when balloon 90 is fully inflated, median section 92 expands against the vessel wall, thereby expanding stent 913 mounted thereon. In this position, stent 913 is released from sleeves 915, is fully deployed and capable of maintaining the patency of lumen 905.

Advantageously, and due at least in part to the preferential expansion of cone sections 94, prior to any significant expansion of median section 92 and/or stent 913, any potential shifting of stent 913 within lumen 905 that might otherwise occur, can be reduced or eliminated, and as a result, a more robust stent delivery can be obtained. Further, the preferential expansion of cone sections 94 beneficially aids in the release of stent 913 from sleeves 915.

The use of stent delivery system 900 in the delivery of stents comprised of a flexible material is particularly advantageous in that such flexible stents typically expand when introduced into the body, thereby rendering release from socks 915 difficult. However, the stent, balloon, and balloon catheter of stent delivery system 900 may be formed of any material, as described hereinabove.

Sleeves 915 may be formed of any material and by any known method. Non-limiting examples of sleeves, and the materials and methods of making sleeves, are disclosed in U.S. Pat. Nos. 4,950,227; 5,944,726; and 5,980530; the entire disclosures of which are incorporated herein by reference for all purposes.

The balloon 90, stent 913 and stent delivery system 900 may be manufactured by any suitable method, as described hereinabove. Furthermore, stent delivery systems comprising sleeves, and methods of manufacturing the same are known, and are described in, for example, U.S. Pat. No. 4,950,227, the entire disclosure of which is hereby incorporated by reference for all purposes.

The discovery of the advantages of the herein disclosed ratio between the cone volume and the cross sectional area of a balloon, when applied to a catheter balloon embodying the features of the invention, results in a catheter balloon that can expand in a controllable fashion. The inventive catheter balloon is advantageously employed as a component of balloon catheter systems and stent delivery systems, as described above. When utilized in such systems, the inventive balloon provides the advantages of decreased shifting the median section of the balloon and/or of a stent mounted thereon, and enhanced release of a stent from sleeves, or socks, if the same are provided on the inventive stent delivery system. The inventive balloon, balloon catheter, and stent delivery system thus provide advantages when utilized to treat a patient. As a result, the present invention further provides methods of dilating a bodily lumen, as well as a methods of delivering a stent, or other prosthetic device.

The inventive method of dilating a lumen generally comprises the steps of providing a balloon catheter, wherein the balloon catheter comprises at least a balloon embodying the features of the present invention. The balloon catheter is inserted into the lumen and the balloon advanced to the site that is desirably dilated. The balloon is then inflated to cause the radial expansion of the balloon and the dilation of the lumen. The balloon may then be deflated and withdrawn from the lumen.

The inventive method of delivering a stent or other prosthetic device, generally comprises the steps of providing a stent delivery device, wherein the stent delivery device comprises at least a balloon embodying features of the invention. The stent delivery system is inserted into the lumen and the stent directed to the site where it is desirably delivered. Once so positioned, the balloon is inflated, during which inflation the cone sections inflate prior to any significant expansion of the median section thereof. The median section, as well as the stent mounted thereon then expand until the stent reaches the lumen wall. Because the cone sections preferentially inflate prior to any significant expansion of the median section of the balloon and/or the stent mounted thereon, the cone sections can reduce any shifting of the stent from the desired delivery site that may otherwise occur. Once so delivered, the stent would be capable of maintaining the patency of the lumen wall. The balloon may then be deflated and removed from the bodily lumen.

A stent delivery system in accordance with the present invention may be utilized to deliver stents to, for example, coronary arteries, peripheral arteries, and visceral arteries as well as to the biliary, urinary, respiratory, reproductive or gastrointestinal tracts. Further, although stents are mentioned with particularity, and delivery system of the present invention can be utilized to deliver any prosthetic device suitably delivered with an inflatable member.

Numerous characteristics and advantages of the invention described by this document have been set forth in the foregoing description. It is to be understood, however, that while particular forms or embodiments of the invention have been illustrated, various modifications, including modifications to shape, and arrangement of parts, and the like, can be made without departing from the spirit and scope of the invention.

What is claimed is:

1. A catheter balloon comprising:
   a median section having a proximal and distal end and a transverse cross sectional area in mm$^2$ when the balloon is inflated;
   a first cone section proximal to the proximal end of the median section and a second cone section distal to the distal end of the median section, each such first and second cone sections having a volume in mm$^3$ when the balloon is inflated, wherein the ratio of the volume of either of the cone sections to the transverse cross sectional area of the median section of at least about 2.1 mm; and
   wherein at least one of such cone sections comprises a stepped configuration comprising a plurality of sections and wherein at least one of the plurality of sections defines an internal angle relative to the median section of greater than 180 degrees and the median section having a diameter greater than the at least one of such cone sections comprising a stepped configuration.

2. The catheter balloon of claim 1, wherein the ratio of the volume of either of the cone sections to the transverse cross sectional area of the median section is from about 2.1 mm to about 4.0 mm.

3. The catheter balloon of claim 2, wherein the ratio of the volume of either of the cone sections to the transverse cross sectional area of flue median section is from about 2.1 mm to about 2.5 mm.

4. A balloon catheter comprising:
   an elongated shaft having a proximal end, a distal end, and an inflation lumen extending through at least a section thereof and
   a catheter balloon mounted on a distal shaft section having an interior in fluid communication with the inflation lumen and further comprising
      a median section having a proximal and distal end and a transverse cross sectional area in mm$^2$ when the balloon is inflated;
      a first cone section proximal to the proximal end of the median section and a second cone section distal to the distal end of the median section, each such first and second cone sections having a volume in mm$^3$ when the balloon is inflated, wherein the ratio of the volume of either of the cone sections to the transverse cross sectional area of the median section of at least about 2.1 mm; and
      wherein at least one of such cone sections comprises a stepped configuration comprising a plurality of sections and wherein at least one of the plurality of sections defines an internal angle relative to the median section of greater than 180 degrees and the median section having a diameter greater than the at least one of such cone sections comprising a stepped configuration.

5. The balloon catheter of claim 4, wherein the ratio of the volume of either of the cone sections to the transverse cross sectional area of the median section is from about 2.1 mm to about 4.0 mm.

6. The balloon catheter of claim 5, wherein the ratio of the volume of either of the cone sections to the transverse cross sectional area of the median section is from about 2.1 mm to about 2.5 mm.

7. The balloon catheter of claim 5, further comprising an expandable stent disposed about at least a portion of the median section of the catheter balloon.

8. The balloon catheter of claim 7, wherein the expandable stent has an end portion defining a margin between the end portion of the stent and the median section of the catheter balloon and the balloon catheter further comprises a sleeve having a first end mounted on the distal shaft section distal to the catheter balloon and a second end defining a margin between the stent and the sleeve, wherein the sleeve overlies the margin between the stent and the median section of the catheter balloon.

9. The balloon catheter of claim 5 wherein the catheter is a fixed wire catheter.

10. The balloon catheter of claim 5 wherein the catheter is an over-the-wire catheter.

11. The balloon catheter of claim 5 wherein the catheter is a rapid exchange catheter.

12. A method of forming a catheter balloon comprising:
   (a) selecting a material from which to form the balloon;
   (b) forming the balloon so that the balloon comprises
      (i) a median section having a proximal and distal end and a transverse cross sectional area in mm$^2$ when the balloon is inflated; and
      (ii) a first cone section proximal to the proximal end of the median section and a second cone section distal to the distal end of the median section, each such first and second cone sections having a volume in mm$^3$ when the balloon is inflated, wherein the ratio of the volume of either of the cone sections to the transverse cross sectional area of the median section of at least about 2.1 mm; and
      (iii) wherein at least one of such cone sections comprises a stepped configuration comprising a plurality of sections and wherein at least one of the plurality of sections defines an internal angle relative to the median section of greater than 180 degrees and the median section having a diameter greater than the at least one of such cone sections comprising a stepped configuration.

13. The method of claim 12, wherein the ratio of the volume of either of the cone sections to the transverse cross sectional area of the median section is from about 2.1 mm to about 4.0 mm.

14. The balloon catheter of claim 13, wherein the ratio of the volume of either of the cone sections to the transverse cross sectional area of the median section is from about 2.1 mm to about 2.5 mm.

15. A method for dilating a bodily lumen within a patient's body comprising:
   (a) providing a balloon catheter, comprising
      (i) an elongated shaft having a proximal end, a distal end, and an inflation lumen extending with at least a section thereof; and
      (ii) a catheter balloon mounted on the distal shaft section having an interior in fluid communication with the inflation lumen, the balloon comprising a median section having a proximal and distal end and a transverse cross sectional area in mm$^2$ when the balloon is inflated; and
      a first cone section proximal to the proximal end of the median section and a second cone section distal to the distal end of the median section, each such first and second cone sections having a volume in mm$^3$ when the balloon is inflated, wherein the ratio of the volume of either of the cone sections to the transverse cross sectional area of the median section of at least about 2.1 mm;
      wherein at least one of such cone sections comprises a stepped configuration comprising a plurality of sections and wherein at least one of the plurality of sections defines an internal angle relative to the median section of greater than 180 degrees and the median section having a diameter greater than the at least one of such cone sections comprising a stepped configuration;

(b) inserting the balloon catheter into bodily lumen of the patient's body to be dilated;

(c) inflating the balloon so that the median section expands to dilate the bodily lumen.

16. A method for delivering a stent to a bodily lumen within a patient's body comprising:

(a) providing a stent delivery system, comprising (i) an elongated shaft having a proximal end, a distal end, and an inflation lumen extending with at least a section thereof;

(ii) a catheter balloon mounted on the distal shaft section having an interior in fluid communication with the inflation lumen, the balloon comprising:

a median section having a proximal and distal end and a transverse cross sectional area in $mm^2$ when the balloon is inflated; and a first cone section proximal to the proximal end of the median section and a second cone section distal to the distal end of the median section, each such first and second cone sections having a volume in $mm^3$ when the balloon is inflated, wherein the ratio of the volume of either the cone sections to the transverse cross sectional area of the median section of at least about 2.1 mm;

(iii) wherein at least one of such cone sections comprises a stepped configuration comprising a plurality of sections and wherein at least one of the plurality of sections defines an internal angle relative to the median section of greater than 180 degrees and the median section having a diameter greater than the at least one of such cone sections comprising a stepped configuration;

(iv) an expandable stent disposed about at least a portion of the median section of the balloon;

(b) inserting the stent delivery system into the bodily lumen of the patient's body;

(c) inflating the balloon to produce the radial expansion of the median section and the stent disposed thereon, thereby delivering the stent.

17. The method of claim 16, wherein the stent delivery system further comprises a sleeve having a first end mounted on the distal shaft section distal to the catheter balloon and a second end defining a margin between the stent and the sleeve, wherein the sleeve overlies the margin between the stent when the catheter balloon is substantially uninflated and the inflation of the balloon further causes the second end of the sleeve to retract so that the sleeve no longer covers the stent and delivering the stent.

* * * * *